(12) United States Patent
Foulger et al.

(10) Patent No.: US 6,900,432 B1
(45) Date of Patent: May 31, 2005

(54) FIRE DETECTION METHOD

(75) Inventors: Brian Foulger, Dorchester (GB); James Riches, Salisbury (GB); Hilary Roberta Bollan, Bristol (GB)

(73) Assignee: The Secretary of State for Defence, Salisbury (GB)

( * ) Notice: Subject to any disclaimer, the term of this patent is extended or adjusted under 35 U.S.C. 154(b) by 0 days.

(21) Appl. No.: 09/889,639

(22) PCT Filed: Jan. 25, 2000

(86) PCT No.: PCT/GB00/00210
§ 371 (c)(1),
(2), (4) Date: Dec. 4, 2001

(87) PCT Pub. No.: WO00/45354
PCT Pub. Date: Aug. 3, 2000

(30) Foreign Application Priority Data

Jan. 28, 1999 (GB) ............................................. 9901764

(51) Int. Cl.$^7$ ............................ B01D 59/44; H01J 49/00
(52) U.S. Cl. ..................... 250/287; 250/281; 250/282; 340/628; 340/632
(58) Field of Search ............................. 250/281, 282, 250/287, 288, 286; 340/506, 628, 632; 436/52, 106, 178

(56) References Cited

U.S. PATENT DOCUMENTS

| 4,053,776 | A |   | 10/1977 | Hertzberg et al. |       |
|-----------|---|---|---------|------------------|-------|
| 4,633,082 | A |   | 12/1986 | Sauers           |       |
| 4,691,783 | A |   | 9/1987  | Stern et al.     |       |
| 4,820,920 | A | * | 4/1989  | Bather ........................ | 250/282 |
| 5,065,140 | A | * | 11/1991 | Neuburger .................... | 340/634 |
| 5,162,652 | A |   | 11/1992 | Cohen et al.     |       |
| 5,294,794 | A |   | 3/1994  | Davies           |       |
| 5,300,773 | A | * | 4/1994  | Davies ........................ | 250/286 |
| 5,310,681 | A | * | 5/1994  | Rounbehler et al. ......... | 436/106 |
| 5,371,364 | A | * | 12/1994 | Davies et al. ................ | 250/287 |
| 5,376,924 | A | * | 12/1994 | Kubo et al. .................. | 340/632 |
| 5,405,781 | A | * | 4/1995  | Davies et al. ................. | 436/52 |
| 5,585,575 | A | * | 12/1996 | Corrigan et al. .......... | 73/863.71 |
| 5,653,539 | A | * | 8/1997  | Rosengaus .................... | 374/159 |
| 5,859,375 | A | * | 1/1999  | Danylewych-May et al. ........................ | 73/864.71 |
| 6,087,183 | A | * | 7/2000  | Zaromb ....................... | 436/178 |

FOREIGN PATENT DOCUMENTS

| EP | 0401861 | 12/1990 |
| EP | 0795749 | 9/1997 |
| GB | 926605 | 5/1963 |
| GB | 1571963 | 7/1980 |
| GB | EP 0551722 A1 * | 11/1992 |
| WO | WO 97/05635 | 2/1997 |

* cited by examiner

Primary Examiner—John R. Lee
Assistant Examiner—Paul M. Gurzo
(74) Attorney, Agent, or Firm—Dean W. Russell; Kilpatrick Stockton LLP

(57) ABSTRACT

A method for detecting gases or vapors emitted from materials, such as electrical components, under conditions at which there is a risk of the onset of fire, said method comprising sampling gas from the region of the material using an ion mobility spectrometer tuned to detect specific volatilized materials. The signal can be used to determine a fire risk and to trigger alarms as necessary. The method provides rapid detection with high sensitivity and high selectivity so as to minimize false alarms. Apparatus for use in the method is also described and claimed.

7 Claims, 3 Drawing Sheets

Ion Intensity/ Arbitrary units

Ion drift time / ms

Ion Intensity/ Arbitrary units

Ion drift time / ms

FIRE DETECTION METHOD

This application claims priority to United Kingdom Application No. 9901764.2 filed on Jan. 28, 1999 and International Application No. PCT/GB00/00210 filed on Jan. 25, 2000 and published in English as International Publication No. WO 00/45354 on Aug. 3, 2000.

The present invention relates to a method for the detection of overheating of materials in particular electrical equipment, which precedes the onset of fire, as well as to apparatus for use in the method. Thus the invention is useful in providing advance warning of conditions likely to lead to fire so that preventative action can be taken.

Early warning fire detectors often rely on the detection of smoke particles to trigger an alarm. At this stage, fire is imminent if not already underway and so it is generally too late for preventative action.

Methods for the early detection of fire based upon the vapour detection have also been described. These have potential to provide advanced warning of an imminent fire. These chemical sensing techniques are often based on chemical coatings which interact with the outgassing vapours either through a chemical reaction (U.S. Pat. No. 5,065,140) or adsorption. In the former case, the detector lacks versatility in that it reacts only to the vapour of interest. The latter method lacks specificity and requires considerable signal processing effort.

Ion mobility spectrometers are well known in the detection of chemical warfare agents, explosives, propellants, and industrial pollutants. The principles by which they operate and the design of spectrometers are described for example by W. Carr (Ed). "Plasma Chromatography", Plenum Press, London, 1984, and Turner et al., Trends in Analytical Chemistry, 13, 7 (1994) 275–280. In essence, an ion mobility spectrometer consists of an ionisation region coupled to an ion drift tube via a shutter grid. A sample is introduced into the ionisation region together with a carrier gas (such as air), for example using a suction pump. In the ionisation region, the carrier gas molecules (as well as any sample) are ionised by beta radiation from a Ni-63 radioactive source, or other methods such as corona discharge or photoionisation. Reactant ions are produced from the carrier gas (such as air) which react with the sample gas, generally in a complex manner, so as to result in product ions. Under the influence of an applied electric field, reactant and product ions are extracted from the ionisation region into the ion drift region. In the ion drift region, the ions separate due to their different mobilities determined by their size, charge and polarisability. They are collected at a collector electrode where they are neutralised, and so generate an electric current that can be measured. Data is generated at a rapid rate. Repeat scans are suitably averaged to improve the signal to noise ratio.

The spectrometer can be arranged to detect either positive or negative ions by reversal of the voltages.

The present invention provides a method for detecting gases or vapours emitted from materials under conditions at which there is a risk of the onset of fire, said method comprising sampling gas from the region of the material using an ion mobility spectrometer, detecting the ion peaks of volatilised material.

The advantages of the use of ion mobility spectrometry in this application are associated with its extreme sensitivity and selectivity. The spectrometer can be pre-set, by controlling the potentials applied to the drift region for example, so as to detect selected target gases which are emitted during outgassing through heating in any specific environment. The selectivity of the device means that it could be applied to a variety of different environments. However, it will be particularly useful in high technology environments, such as data processing and computer facilities, telephone exchanges, space stations, industrial plants especially chemical plants or plants which deal with inflammable materials, where the risk of fire as a result of overheating devices and in particular electrical components is high, and the consequences of such a fire are extreme in economic terms at least.

Sampling can take place either continuously or at intervals, for example at pre-set intervals. Preferably, the sampling will be carried out continuously, as this allows an increasing signal, produced as a result of increased outgassing of a particular gas from the materials, for example as the temperature rises, to be detected against background noise levels.

The spectrometer may be connected to a warning or alarm system that may be triggered automatically, using various predetermined parameters. For example, if a signal peak reaches a particular intensity, this may trigger the alarm. An alternative, particularly suitable with continuous monitoring, would be to arrange for the alarm to be triggered when any signal peak increases significantly over a period of time. This may be indicative of a rise in temperature of the component that gives rise to the particular gas or vapour.

The alarm may be connected to the detection of features characteristic of thermal degradation and not just simple over-heating of components. This would ensure that only potentially serious situations resulted in an actual alarm, reducing false positives to a minimum.

The levels and the parameters used to trigger the alarm will vary depending upon the particular circumstances in which the spectrometer is being employed. Again, these can be determined using routine methods and the control systems designed appropriately.

There is no need to know or analyse the materials which are emitted, provided it can be ensured that at least some of these fall within the detection range set on the ion mobility spectrometer. This can be done by routine methods. For example, one or more representative components present in the particular environment to be monitored can be heated under safe test conditions and the signal generated as a result of the emission of material monitored. The detection range of the ion mobility spectrometer can then be adjusted to ensure a signal is generated under these conditions.

The spectrometer will be pre-set to detect either positive or negative ions depending upon the nature of the signal in each case. Selection of the most sensitive signal in each particular case can be determined, again by routine methods.

Many solid materials that release volatile material when heated, but in particular are electrical components such as printed circuit boards, resistors and lacquer-coated materials. The spectrometer will suitably be set to detect vapours emitted from such components.

Available ion mobility spectrometers are convenient to use in that it is small and hand-held. For use in the context of the invention however, size and portability may be less critical. The spectrometer may be installed in the environment on a permanent basis. It would not, under these circumstances be required to be as robust as a device which is intended, for example to be carried onto a battle-field. This may result in cost savings in the spectrometer itself.

In a further aspect the invention provides apparatus for detecting a heightened fire risk in an environment using the method as described above.

In particular, the apparatus will comprise an ion mobility spectrometer. The spectrometer is suitably adapted such that it is able to detect increases in the particular gases of vapours emitted from materials present in the particular environment in which it is placed, under conditions at which there is a heightened risk of the onset of fire. In particular, the controls of the device will be pre-set so that they are able to detect specific volatile materials likely to be emitted from materials present in the particular environment, which presents a potential fire hazard.

The precise settings of the controls of the spectrometer will vary depending upon the particular environment being monitored and can be determined by the skilled person using routine methods. Typically the electric field applied to the drift tube of the device will be in the range of from 150 to 350V/cm, more usually from 200 to 300V/cm and often at about 250V/cm. The frequency of spectrometer readings necessary to provide a rapid, detectable signal will depend to some extent, on the ion drift times of the particular volatile materials being detected. Generally, these are less than 20 ms, and so spectra may be gathered at the rate of between 40 to 60 Hz, for example at about 50 Hz.

Thus in a particular embodiment of the invention, there is provided an ion mobility spectrometer for use, or when used, in the method described above.

Yet a further aspect of the invention provides the use of an ion mobility spectrometer for the detection of a heightened risk of fire in an environment. More particularly, there is provided, the use of an ion mobility spectrometer in the detection of gases or vapours emitted from materials under conditions at which there is a risk of the onset of fire.

The invention will now be particularly described by way of example with reference to the accompanying diagrammatic drawings in which.

Figure 1:
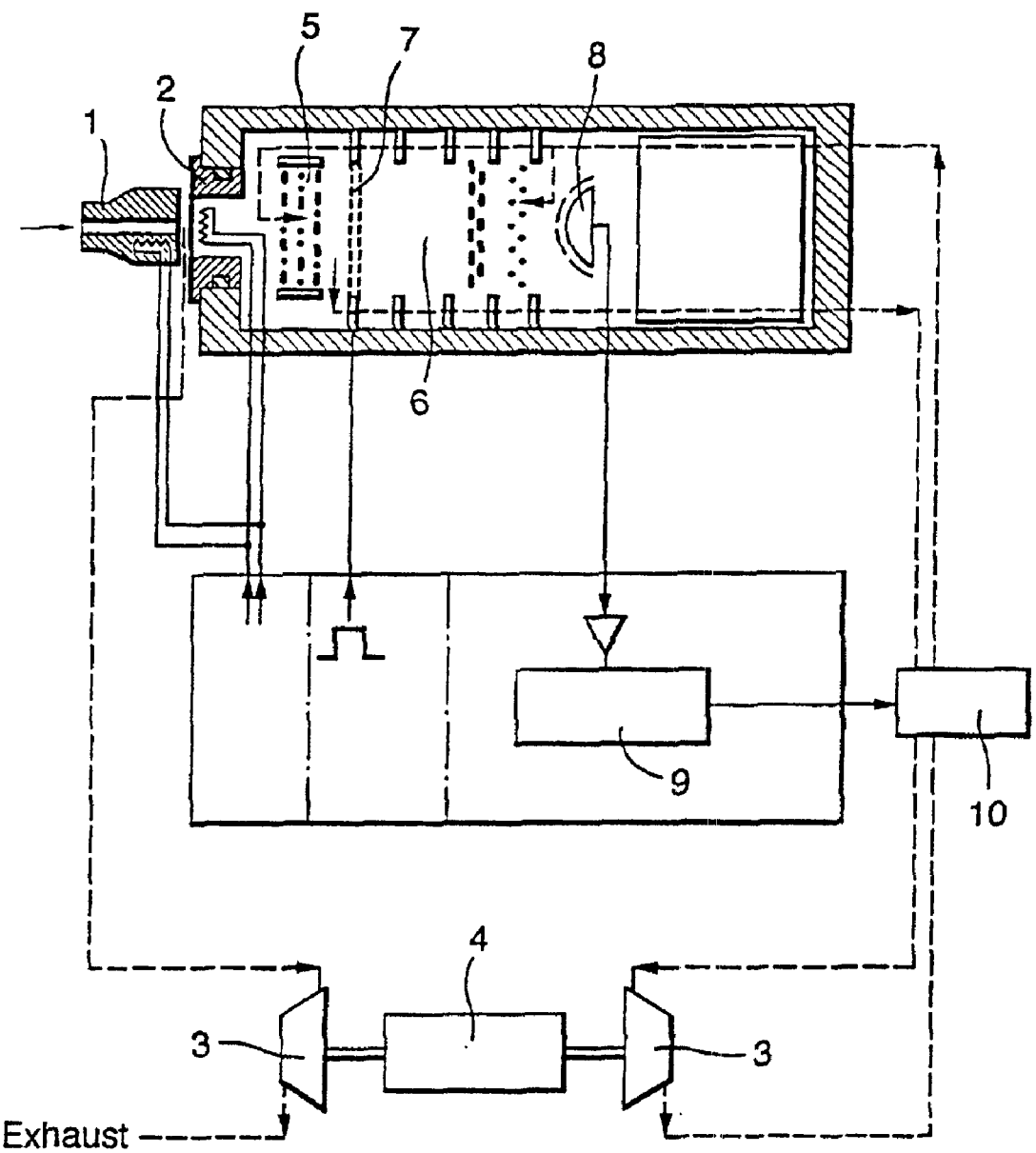
FIG. 1 is a schematic diagram of an ion mobility spectrometer.

The illustrated device in FIG. 1 comprises an inlet system comprising a heated nozzle (1) and a silicon rubber membrane (2). Gas sample is admitted through the inlet system as a result of the action of a diaphragm pump (3) operated by a motor (4). Sample transfers into an ionisation section (5) where a nickel-63 ion source generates the ions. A pulse of ions (generally about 0.2 ms) is admitted into a drift tube section (6) by manipulation of the potentials on a grid assembly (7). The drift tube (6) is typically about 4 cm long with an electric field of 250V/cm. Ions pass to a collector electrode (8), where they are neutralised, generating a current which is passed to a microprocessor (9), which generates a signal, if necessary after amplification. The signal may be passed to a display assembly (10).

In general ion drift times are less than 20 ms, and so spectra may be gathered at the rate of say 50 Hz.

EXAMPLE 1

Figure 2:
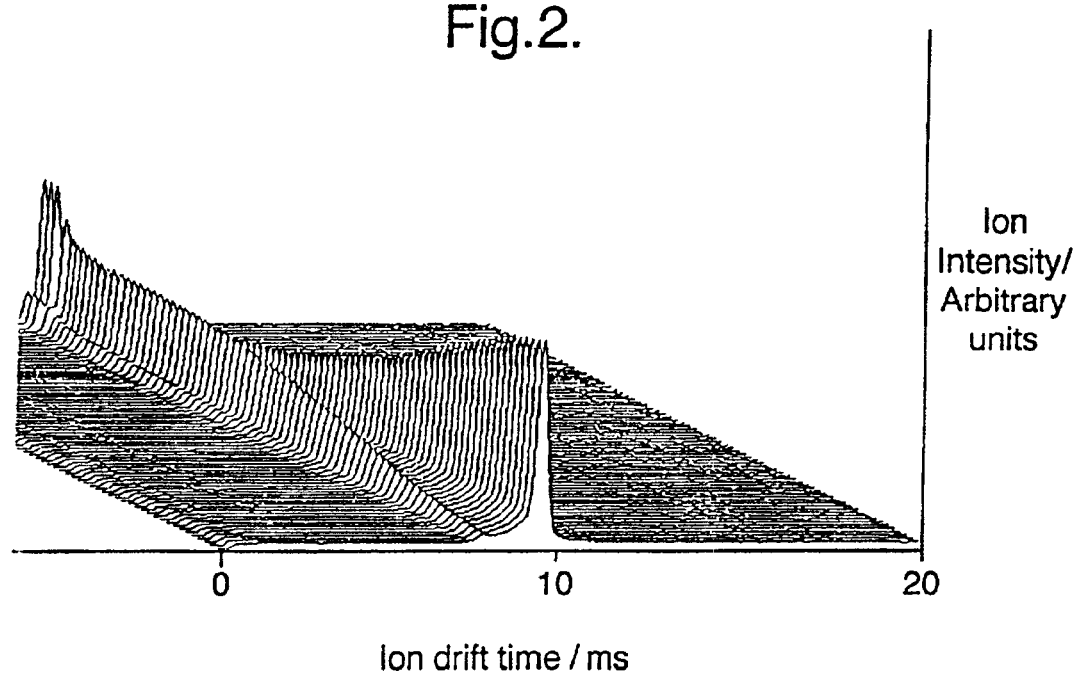
FIG. 2 shows the positive ion mobility spectra for a heated lacquer-coated printed circuit board at temperatures of from 50 to 85° C.
Figure 3:
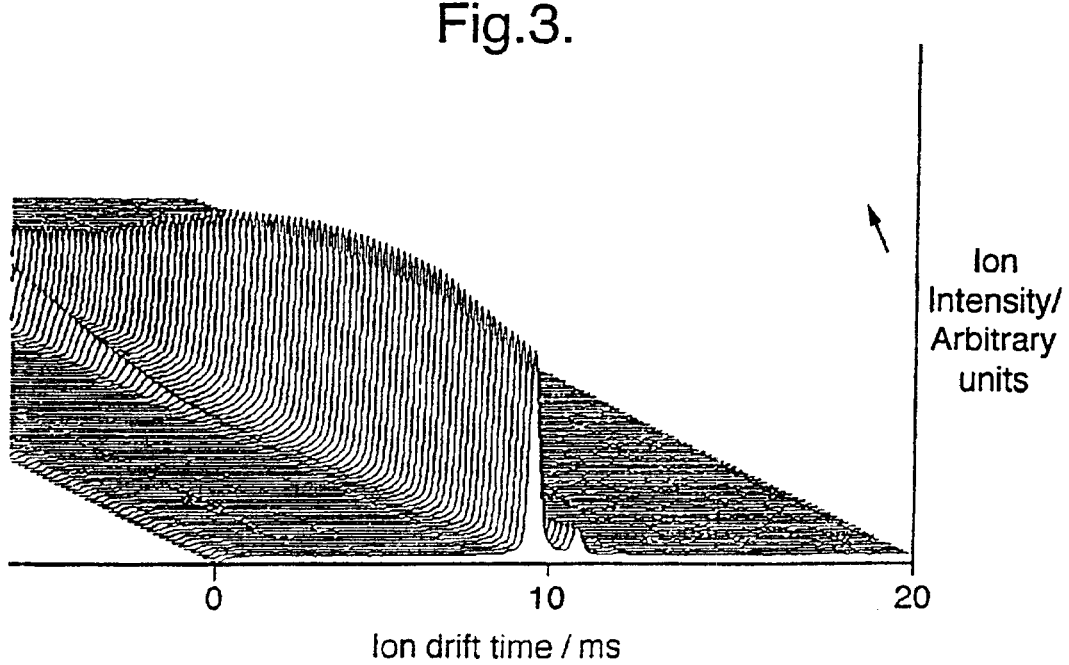
FIG. 3 shows the positive ion mobility spectra for a heated lacquer-coated printed circuit board at temperatures of from 85 to 105° C.

A lacquer coated printed circuit board was heated from 50 to 105° C. in the vicinity of an ion mobility spectrometer that was operational throughout. At the start of the heating process, the positive reactant ion peak (i.e. that produced as a result of the ionisation of air), is the major feature of the spectrum (see FIG. 2—trace at the back of the representation). As the printed circuit board was heated, this peak is replaced by an ion of reduced mobility (further to the right in the representation), formed by the reaction of vapour emitted by the board with reactant ions in the instrument. This characteristic feature increases in intensity and then falls as a further prominent ion is formed (FIG. 3).

EXAMPLE 2

Figure 4:
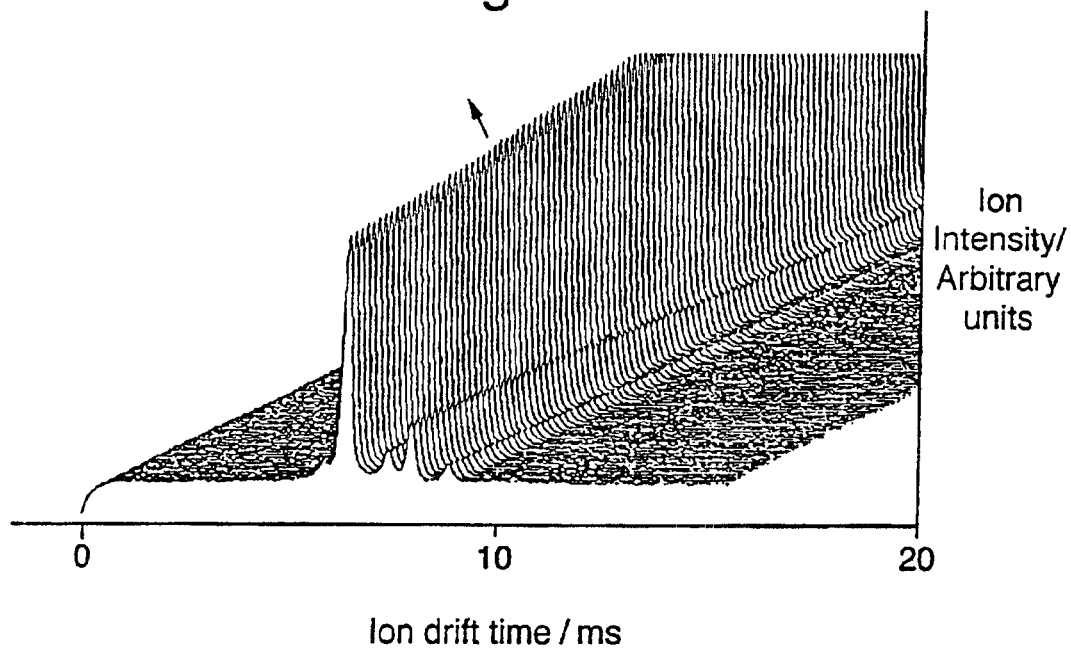
FIG. 4 shows the negative ion mobility spectra for a resistor heated to 50 to 100° C.
Figure 5:
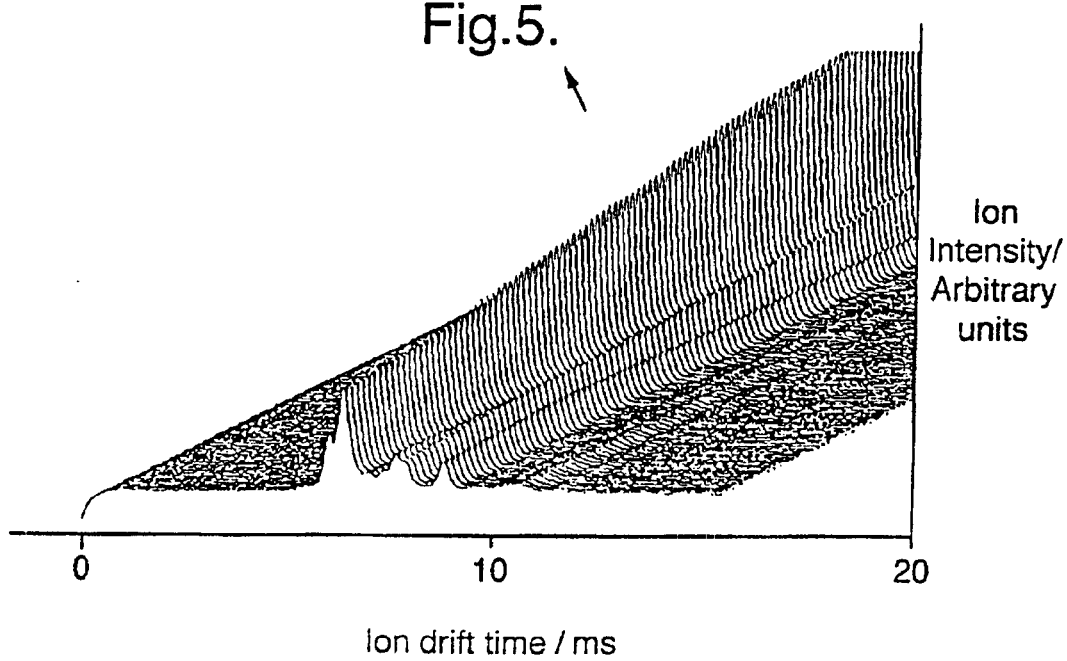
FIG. 5 shows the positive ion mobility spectra for a resistor heated to 50 to 100° C.

Example 1 was repeated but this time with a resistor in place of the printed circuit board. In a first experiment, the resistor was heated from 50 to 100° C. and in a second experiment, a temperature range of from 90 to 140° C. was used. Significant changes in the negative ion spectra (FIGS. 4 and 5 respectively) were recorded.

The sensitivity of this technique is clear from this example, as resistors do not generally emit volatile materials.

What is claimed is:

1. A method for detecting a heightened risk of the onset of fire of an electrical component comprising the steps of sampling the atmosphere around the component using an ion mobility spectrometer and detecting a change in the ion mobility spectrum that is characteristic of overheating of the component.

2. A method according to claim 1, in which the change is indicative of an increase in the emission of a target gas or vapour from the component.

3. A method according to claim 2, comprising the further step of triggering an alarm on detecting the change.

4. A method according to claim 2, in which the component is a printed circuit board or a resistor.

5. A method according to claim 1, comprising the further step of triggering an alarm on detecting the change.

6. A method according to claim 5, in which the component is a printed circuit board or a resistor.

7. A method according to claim 1, in which the component is a printed circuit board or a resistor.

* * * * *